(12) United States Patent
Homma (10) Patent No.: US 12,414,809 B2
(45) Date of Patent: Sep. 16, 2025

(54) TREATMENT TOOL FOR ENDOSCOPE

(71) Applicant: Kiyoaki Homma, Yamagata (JP)

(72) Inventor: Kiyoaki Homma, Yamagata (JP)

( * ) Notice: Subject to any disclaimer, the term of this patent is extended or adjusted under 35 U.S.C. 154(b) by 940 days.

(21) Appl. No.: 17/533,483

(22) PCT Filed: Jun. 19, 2019

(86) PCT No.: PCT/JP2019/024203
§ 371 (c)(1),
(2) Date: Nov. 23, 2021

(87) PCT Pub. No.: WO2020/255278
PCT Pub. Date: Dec. 24, 2020

(65) Prior Publication Data
US 2022/0183739 A1     Jun. 16, 2022

(51) Int. Cl.
*A61B 17/00*     (2006.01)
*A61B 1/015*     (2006.01)
(Continued)

(52) U.S. Cl.
CPC .............. *A61B 18/12* (2013.01); *A61B 1/015* (2013.01); *A61B 2017/0046* (2013.01); *A61M 39/1011* (2013.01)

(58) Field of Classification Search
CPC .. A61B 1/018; A61B 1/015; A61B 2017/0034
See application file for complete search history.

(56) References Cited

U.S. PATENT DOCUMENTS 5,704,914 A * 1/1998 Stocking ........... A61M 25/0606
604/195
2005/0033354 A1 2/2005 Montalvo et al.
(Continued)

FOREIGN PATENT DOCUMENTS

CN     105813685 A     7/2016
CN     206093265 U     4/2017
(Continued)

OTHER PUBLICATIONS

English translation of JP-2000217831 (Iwasaki).*
(Continued)

*Primary Examiner* — Courtney B Fredrickson
(74) *Attorney, Agent, or Firm* — BACON & THOMAS, PLLC (57) ABSTRACT

A treatment tool for an endoscope includes an elongated cylindrical flexible sheath, an operation wire inserted into a cylinder of the flexible sheath and movable forward and backward in an axial direction within the cylinder by being operated to be pushed and pulled, a treatment unit provided in a distal end of the operation wire and performing treatment of an affected area, an operation unit for operating the operation wire to move forward and backward, and a liquid injection unit arranged between the flexible sheath and the operation unit and including a liquid injection port for supplying liquid to the treatment unit. The liquid injection unit and the operation unit are connected by screw fastening, and a locking mechanism is provided for temporarily fixing the screwed state, thereby preventing a screwed portion between the operation unit and the connection unit from being loosened and disconnected by rotational operation during treatment.

4 Claims, 5 Drawing Sheets

(51) Int. Cl.
  *A61B 18/12* (2006.01)
  *A61M 39/10* (2006.01)

(56) References Cited

U.S. PATENT DOCUMENTS

| | | |
|---|---|---|
| 2006/0106349 A1 | 5/2006 | Kito et al. |
| 2016/0354288 A1 | 12/2016 | Uehara et al. |
| 2016/0354594 A1 | 12/2016 | Uehara et al. |

FOREIGN PATENT DOCUMENTS

| | | | |
|---|---|---|---|
| JP | 2000217831 A | * | 8/2000 |
| JP | 2002125978 A | | 5/2002 |
| JP | 2002362082 A | | 12/2002 |
| JP | 2009233269 A | | 10/2009 |
| JP | 2014153461 A | * | 8/2014 |
| JP | 2019122480 A | | 7/2019 |
| KR | 20080096436 A | | 10/2008 |

OTHER PUBLICATIONS

English translation of JP-2014153461 (Kamisaka).*
Chinese First Office Action cited in Chinese Patent Appln. No. 201980097256.X mailed on Oct. 11, 2023.
Extended European Search Report cited in Europan Patent Appln. No. 19934236.1 mailed Dec. 9, 2022.

* cited by examiner

TREATMENT TOOL FOR ENDOSCOPE

TECHNICAL FIELD

The present invention relates to a treatment tool for an endoscope which is inserted into a channel of the endoscope and is provided for performing treatment within a body cavity.

BACKGROUND ART

In general, a treatment tool for an endoscope which is inserted into a channel of the endoscope, and protrudes into a body cavity to perform the treatment is structured such that a treatment unit is arranged in a distal end side of an elongated flexible sheath, and an operation unit is connected to a proximal end side. The operation unit is provided with a liquid injection port for injecting liquid and discharging a radiopaque dye or a drug solution from the distal end side of the flexible sheath into the body cavity.

For example, the following patent literature 1 can be listed up as a literature in which the treatment tool for the endoscope having the operation unit as mentioned above is described.

The technique described in the patent literature 1 can supply the liquid and dispose the liquid by different flow paths by the provision of two or more liquid injection ports or liquid disposal ports communicating with the flow paths in a connection unit connecting a flexible sheath constructed by a multiple lumen tube including a plurality of flow paths and an operation unit. The connection unit is connected in a proximal end side thereof to a distal end of the operation unit by screw fastening. In the present application, a direction toward the operation unit side is called as a proximal end side (or a base end side), and a direction toward the treatment unit is called as a distal end side.

CITATION LIST

Patent Literature

Patent Literature 1: Japanese Unexamined Patent Publication No. 2009-233269

SUMMARY OF INVENTION

Technical Problem

In the treatment tool for the endoscope described in the patent literature 1, the connection unit is connected to the operation unit by screw fastening. Therefore, there has been a problem that a screwed portion is loosened and the connection unit is disconnected when the operation unit is rotationally operated for adjusting a direction of the treatment unit with respect to an affected area within the body cavity, and that a direction of the liquid injection port can not fixed due to slack of the connection unit, thereby making a liquid injecting operation hard.

Further, in order to solve the problem of the slack, an adhesive agent may be used to be firmly fixed. However, in a case where the adhesive agent is used, there has been a problem that the adhesive agent is deteriorated and damaged.

Figure 5A:
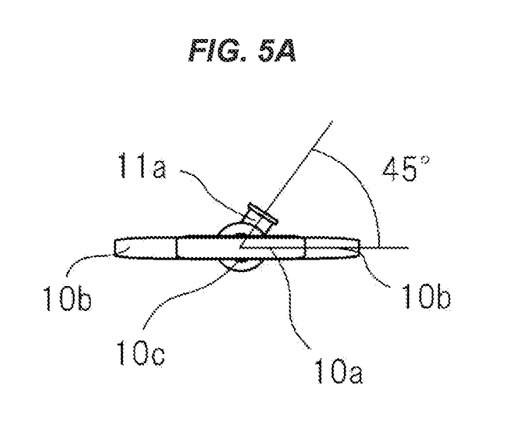
FIGS. 5A and 5B are views for describing an operation of the treatment tool for the endoscope according to the embodiment 1 of the present invention.

In general, the liquid injection port is preferably arranged so as to face to a diagonally side direction of an upper side (a ceiling side when operating) as shown in FIG. 5A as seen from a proximal end side of the operation unit, that is, face to a diagonally upward right direction in a case where an operator is a right-handed operator.

Taking into consideration the problems mentioned above, an object of the present invention is to provide a treatment tool for an endoscope which can prevent a screwed portion between an operation unit and a connection unit from being loosened and disconnected by a rotational operation during treatment, and can temporarily fix a direction of a liquid injection port so as to prevent the liquid injection port from moving from a position where a liquid injecting operation is easily performed.

Solution to Problem

In order to achieve the object mentioned above, according to a first aspect of the present invention, there is provided a treatment tool for an endoscope including an elongated cylindrical flexible sheath, an operation wire which is inserted into a cylinder of the flexible sheath and is movable forward and backward in an axial direction within the cylinder by being operated to be pushed and pulled, a treatment unit which is provided in a distal end of the operation wire and performs treatment of an affected area, an operation unit for operating the operation wire to move forward and backward, a liquid injection unit which is arranged between the flexible sheath and the operation unit and includes a liquid injection port for supplying liquid to the treatment unit, and the liquid injection unit and the operation unit being connected by screw fastening, wherein a locking mechanism is provided for temporarily fixing the screwed state.

Further, according to a second aspect of the present invention, there is provided the treatment tool for the endoscope according to the first aspect, wherein the locking mechanism includes a projection which is arranged in the operation unit and protrudes toward a direction of the liquid injection unit, and a projection which is arranged in the liquid injection unit and protrudes toward a direction of the operation unit, and the projection arranged in one of the operation unit and the liquid injection unit climbs over the other projection by the screwing fastening, thereby temporarily fixing.

Further, according to a third aspect of the present invention, there is provided the treatment tool for the endoscope according to the second aspect, wherein the projection arranged in one of the operation unit and the liquid injection unit is formed into a semispherical shape, the projection arranged in the other of the operation unit and the liquid unit is formed into a rectangular parallelepiped shape which has a long side which is longer than a diameter of the semispherical projection, and is provided in facing surfaces of the operation unit or the liquid injection unit in such a manner that the long side comes into contact with the semispherical projection during the screwing process.

Further, according to a fourth aspect of the present invention, there is provided the treatment tool for the endoscope according to the first aspect, further including a sheath connection unit which is arranged between the flexible sheathe and the liquid injection unit so as to connect the flexible sheath and the liquid injection unit, and a second locking mechanism which connects the sheath connection unit and the liquid injection unit by screw fastening and temporarily fixes the screwed state.

Further, according to a fifth aspect of the present invention, there is provided the treatment tool for the endoscope according to the second aspect, further including a sheath connection unit which is arranged between the flexible sheathe and the liquid injection unit so as to connect the flexible sheath and the liquid injection unit, and a second locking mechanism which connects the sheath connection unit and the liquid injection unit by screw fastening and temporarily fixes the screwed state.

Further, according to a sixth aspect of the present invention, there is provided the treatment tool for the endoscope according to the third aspect, further including a sheath connection unit which is arranged between the flexible sheath and the liquid injection unit so as to connect the flexible sheath and the liquid injection unit, and a second locking mechanism which connects the sheath connection unit and the liquid injection unit by screw fastening and temporarily fixes the screwed state.

Further, according to a seventh aspect of the present invention, there is provided the treatment tool for the endoscope according to the fourth aspect, wherein the second locking mechanism includes a projection which is arranged in the sheath connection unit and protrudes toward a direction of the liquid injection unit, and a projection which is arranged in the liquid injection unit and protrudes toward a direction of the sheath connection unit, and the projection arranged in one of the operation unit and the liquid injection unit climbs over the other projection by the screwing fastening, thereby temporarily fixing.

Further, according to an eighth aspect of the present invention, there is provided the treatment tool for the endoscope according to the fifth aspect, wherein the second locking mechanism includes a projection which is arranged in the sheath connection unit and protrudes toward a direction of the liquid injection unit, and a projection which is arranged in the liquid injection unit and protrudes toward a direction of the sheath connection unit, and the projection arranged in one of the operation unit and the liquid injection unit climbs over the other projection by the screw fastening, thereby temporarily fixing.

Further, according to a ninth aspect of the present invention, there is provided the treatment tool for the endoscope according to the sixth aspect, wherein the second locking mechanism includes a projection which is arranged in the sheath connection unit and protrudes toward a direction of the liquid injection unit, and a projection which is arranged in the liquid injection unit and protrudes toward a direction of the sheath connection unit, and the projection arranged in one of the operation unit and the liquid injection unit climbs over the other projection by the screwing, thereby temporarily fixing.

Further, according to a tenth aspect of the present invention, there is provided the treatment tool for the endoscope according to the seventh aspect, wherein the projection arranged in one of the sheath connection unit and the liquid injection unit is formed into a semispherical shape, the projection arranged in the other of the sheath connection unit and the liquid injection unit is formed into a rectangular parallelepiped shape which has a long side which is longer than a diameter of the semispherical projection, and is provided in facing surfaces of the sheath connection unit or the liquid injection unit in such a manner that the long side comes into contact with the semispherical projection during the screwing process.

Further, according to an eleventh aspect of the present invention, there is provided the treatment tool for the endoscope according to the eighth aspect, wherein the projection arranged in one of the sheath connection unit and the liquid injection unit is formed into a semispherical shape, the projection arranged in the other of the sheath connection unit and the liquid unit is formed into a rectangular parallelepiped shape which has a long side which is longer than a diameter of the semispherical projection, and is provided in facing surfaces of the sheath connection unit or the liquid injection unit in such a manner that the long side comes into contact with the semispherical projection during the screwing process.

Further, according to a twelfth aspect of the present invention, there is provided the treatment tool for the endoscope according to the ninth aspect, wherein the projection arranged in one of the sheath connection unit and the liquid injection unit is formed into a semispherical shape, the projection arranged in the other of the sheath connection unit and the liquid unit is formed into a rectangular parallelepiped shape which has a long side which is longer than a diameter of the semispherical projection, and is provided in facing surfaces of the sheath connection unit or the liquid injection unit in such a manner that the long side comes into contact with the semispherical projection during the screwing process.

Effect of Invention

In the treatment tool for the endoscope according to the present invention, the liquid injection unit and the operation unit are connected by screw fastening, and the locking mechanism is provided for temporarily fixing the screwed state. Therefore, it is possible to prevent the screw fastening portion between the liquid injection unit and the operation unit from being loosened and disconnected during the treatment, and it is possible to temporarily fix the direction of the liquid injection port so as to prevent the liquid injection port from moving from the position where the liquid injection operation is easily performed, thereby easily performing the liquid injection operation.

DESCRIPTION OF EMBODIMENTS

A description will be in detail given below of an embodiment of a treatment tool for an endoscope according to the present invention with reference to the accompanying drawings. First of all, a description will be given of an overall structure of the treatment tool for the endoscope according to the present invention.

Figure 1:
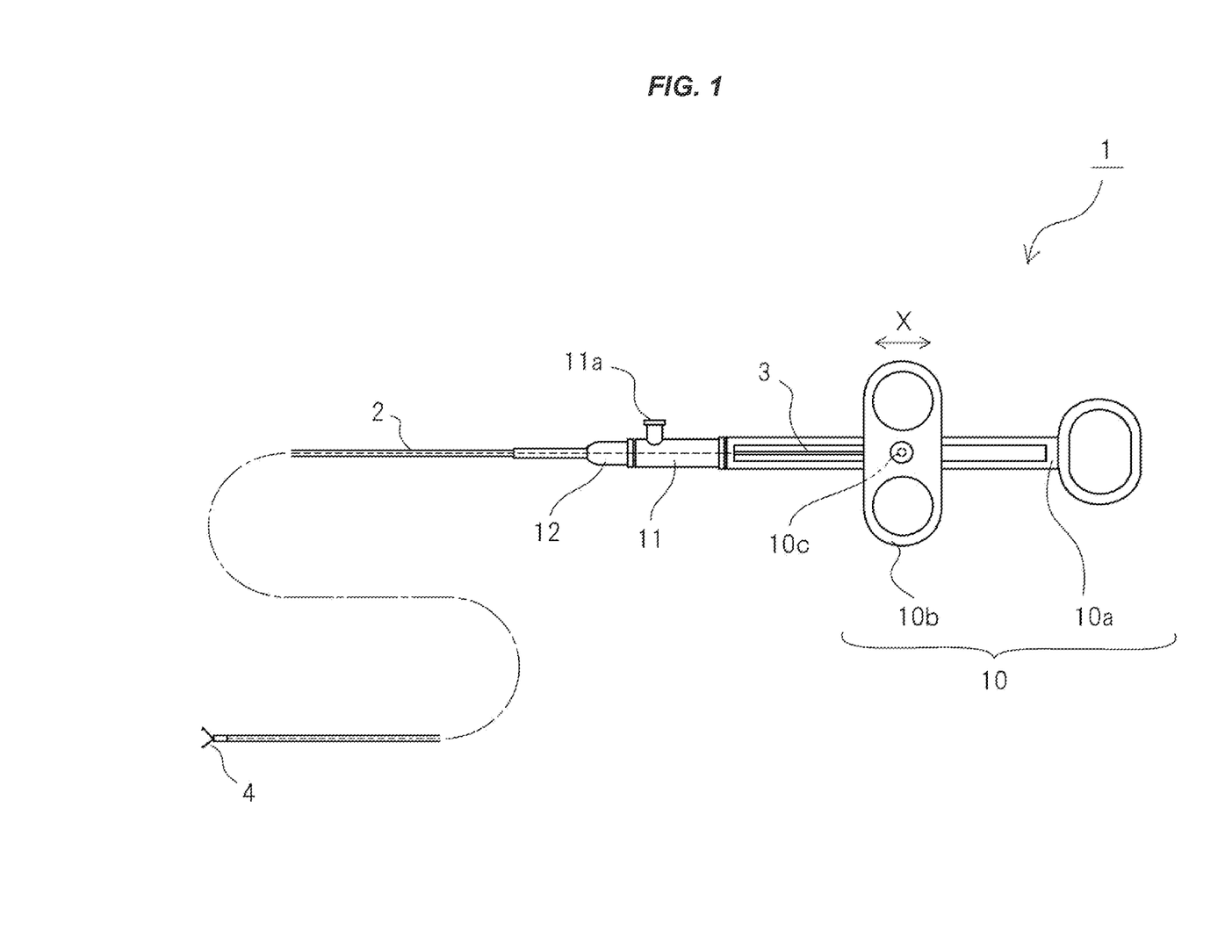
FIG. 1 is a view showing an overall configuration of a treatment tool for an endoscope according to the present invention.

As shown in FIG. 1, a treatment tool 1 for an endoscope according to the present embodiment is provided with an elongated flexible sheath 2 which has an operation unit 10 attached to a proximal end thereof and is made of resin or coil, an operation wire 3 which is inserted into the flexible sheath 2 so as to be movable forward and backward, and a scissors unit 4 which is connected to a distal end of the operation wire 3, is structured such that a pair of distal end electrodes arranged in a distal end of the flexible sheath open and close (open and close in a direction of Y in the drawing) to perform treatment by pushing the operation wire 3 to the distal end side or pulling the operation wire 3 to the proximal end side (operating in a direction of X in the drawing) on the basis of an operation of the operation unit 10 and serves as a treatment unit. The operation unit 10, an injection unit 11 and a sheath connection unit 12 are manufactured by a material such as a synthetic resin which is slightly deformable by weight or pressure.

In the present embodiment, an example in which the treatment unit is constructed by the scissors unit is shown. However, the present invention is not limited to this, but the treatment unit may be constructed by a basket unit which inflates like a basket on the basis of a self-biasing and grips or crushes a foreign substance within the body cavity, and the other treatment units having the other functions.

Further, in the present embodiment, a direction toward the operation unit 10 side in the right of FIG. 1 is called as a proximal end side (or a base end side), and a direction toward the scissors unit 4 serving as the treatment unit is called as a distal end side.

The operation unit 10 is provided with an operation unit body 10a which is arranged in the base end side of the flexible sheath 2 and is gripped by an operator, and a slider 10b which is relatively movable with respect to the operation unit body 10a, and operates the operation wire 3 to move forward and backward by relatively moving the operation unit body 10a and the slider 10b in the direction of X in the drawing, thereby displacing the scissors unit 4 to an open state and a closed state.

The operation wire 3 is covered in a base end side thereof with a reinforcement pipe 16 (FIG. 3) constructed by a stainless pipe so as to prevent the operation wire 3 from being buckled when operating to press.

The slider 10b is provided with a power source connection terminal 10c for connecting a high-frequency power source cord, and can apply a high-frequency current to the scissors unit 4 in the distal end through the operation wire 3.

A liquid injection unit 11 is attached to a distal end of the operation unit 10. A cylindrical liquid injection port 11a is open to the liquid injection unit 11 for a liquid supply of a drug solution to the distal end through an internal portion of the flexible sheath 2 by attachment of an injection syringe (not shown) for injecting the liquid.

Figure 2A:
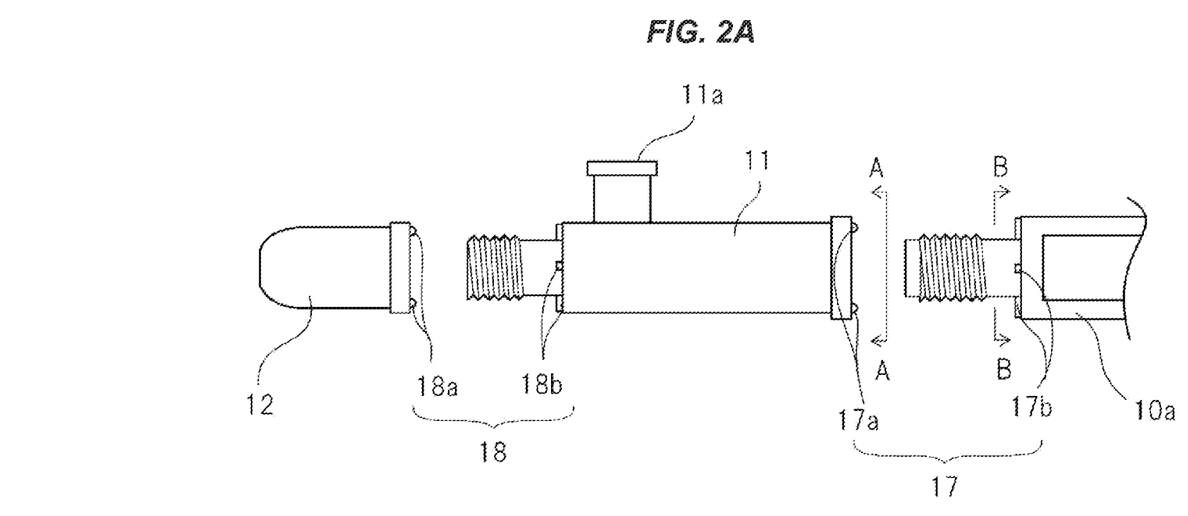
FIGS. 2A to 2D are exploded views of an operation unit of the treatment tool for the endoscope according to an embodiment 1 of the present invention.
Figure 3:
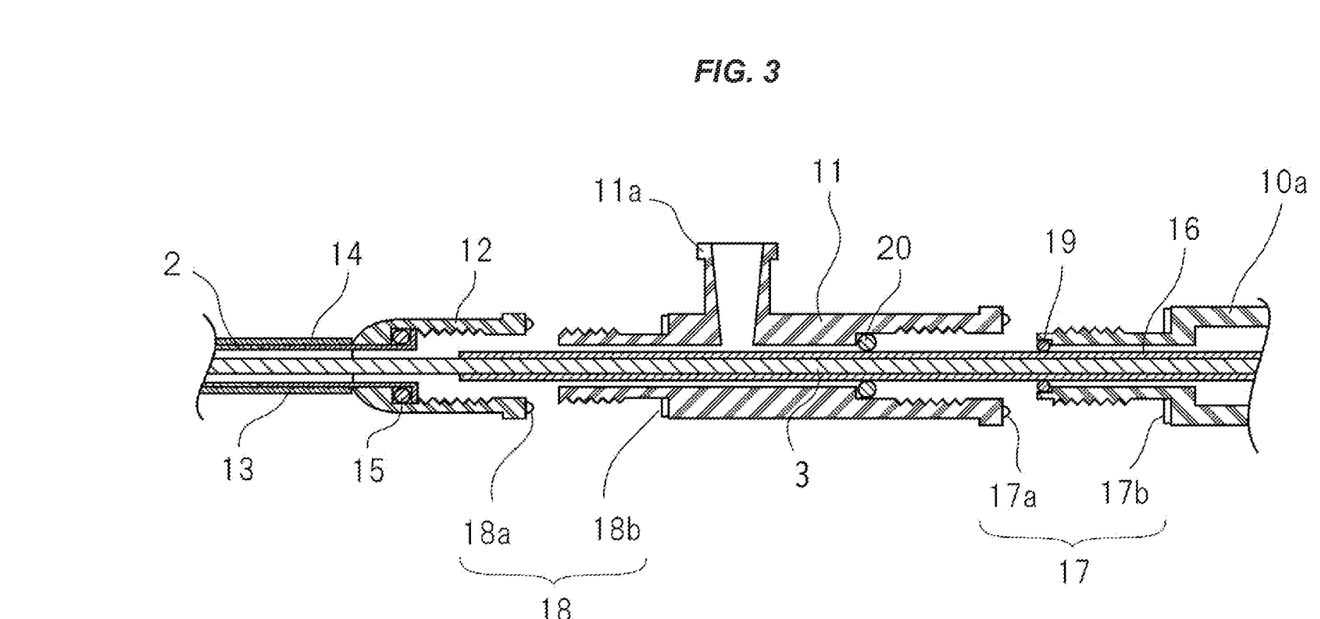
FIG. 3 is a cross sectional view describing an assembly of the operation unit of the treatment tool for the endoscope according to the embodiment 1 of the present invention.
Figure 4:
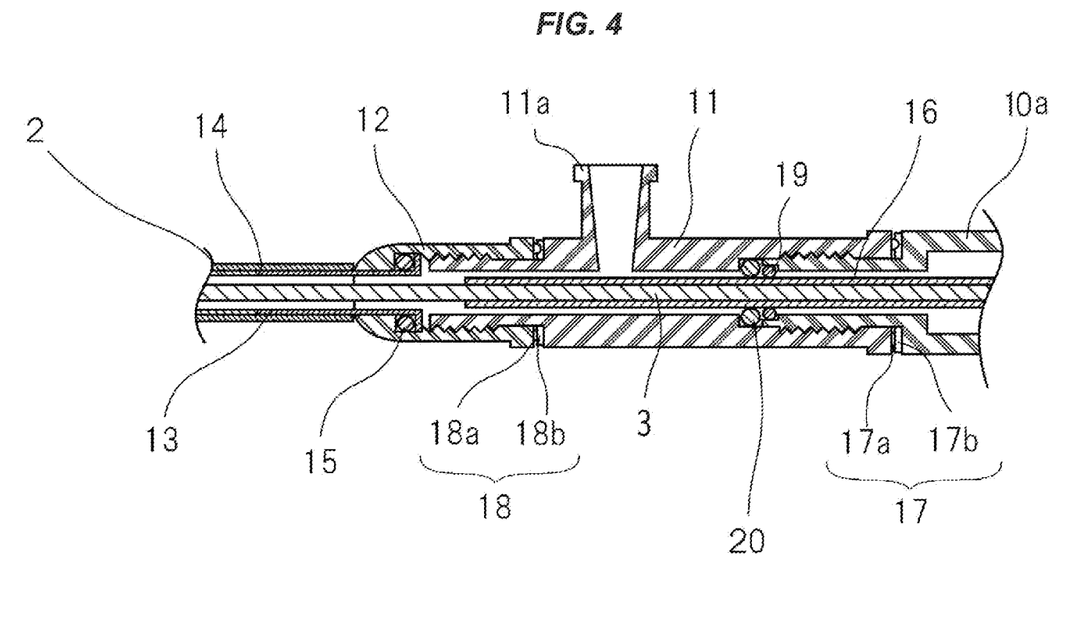
FIG. 4 is a cross sectional view of the operation unit of the treatment tool for the endoscope according to the embodiment 1 of the present invention.

The liquid injection unit 11 is formed into an approximately cylindrical shape having a through hole in an axial direction as shown in an outer appearance diagram in the operation unit side of FIG. 2A (the sheath 2, the operation wire 3 and a folding prevention tube being not shown) and a cross sectional view of FIG. 3, and the liquid injection port 11a for injecting the drug solution is formed to be integrally protruded sideward. The liquid injection port 11a is provided with a hole in a perpendicular direction to the axis of the liquid injection unit 11 in such a manner as to be connected to a through hole in the axial direction of the liquid injection unit 11.

A sheath connection unit 12 for connecting the flexible sheath 2 is connected to the liquid injection unit 11 in a distal end thereof. A through hole is formed in an axial direction of the sheath connection unit 12, and a sheath base end stand 13 for connecting the flexible sheath 2 is arranged in a distal end of the sheath connection unit 12, as shown in FIG. 3. The flexible sheath 2 is connected and fixed to the sheath base end stand 13.

Reference numeral 14 denotes a folding prevention tube which is arranged to surround a base end portion of the flexible sheath 2 and is made of an electric insulating material for preventing the base end portion of the flexible sheath 2 from being sharply folded in the vicinity of the connection portion to the sheath connection unit 12 and being damaged, and reference numerals 15, 19 and 20 denote an O-ring for preventing leakage of liquid.

Next, a description will be given of a connection structure for connecting the operation unit 10 and the liquid injection unit 11.

The connection between the operation unit 10 and the liquid injection unit 11 is achieved by a screwing operation between a female thread which is formed in an inner wall of the liquid injection unit 11 in a proximal end side, and a male thread which is formed in an outer periphery of a small diameter portion having a level difference in a distal end of the operation unit body 10a, as shown in FIGS. 2A to 4. The female thread and the male thread are previously set in such a manner as to be screwed to a predetermined angle mentioned later.

Further, the connection between the sheath connection unit 12 and the liquid injection unit 11 is achieved by a screwing operation between a female thread which is formed in an inner wall of the sheath connection unit 12 in a proximal end side, and a male thread which is formed in an outer periphery of a small diameter portion having a level difference in a distal end of the liquid injection unit 11, as shown in FIGS. 2A to 4.

The treatment tool 1 for the endoscope according to the present embodiment is provided with a first locking mechanism 17 for temporarily fixing a screwed state between the liquid injection unit 11 and the operation unit body 10a, and a second locking mechanism 18 for temporarily fixing a screwed state between the liquid injection unit 11 and the sheath connection unit 12. Next, a description will be given of these locking mechanisms.

Figure 2B:
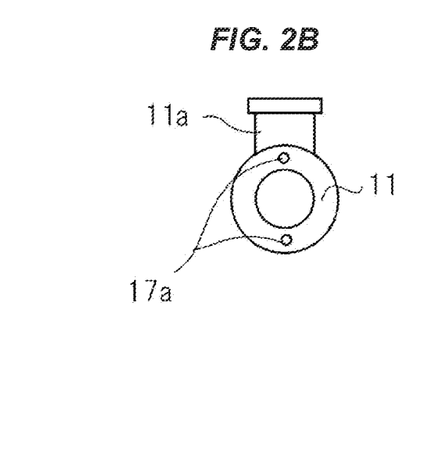
Figure 2C:
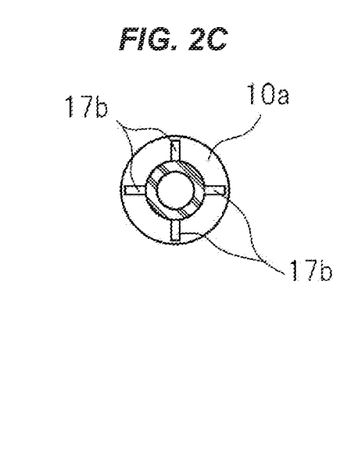

The first locking mechanism 17 is provided with two semispherical projections 17a which protrude toward a direction of the operation unit body 10a from point symmetrical positions on a circumference of a cylindrical end surface of the liquid injection unit 11, shown in FIG. 2B which is a view as seen from a direction of a line A-A in FIG. 2A, and four rectangular parallelepiped projections 17b which extend radially on a cylindrical end surface corresponding to a level difference portion positioned closer to the proximal end side than the male thread of the operation unit body 10a with a longer long side than a diameter of the projection 17a, and protrude toward a direction of the liquid injection unit 11, shown in FIG. 2C which is a view as seen from a direction of a line B-B in FIG. 2A.

Figure 2D:
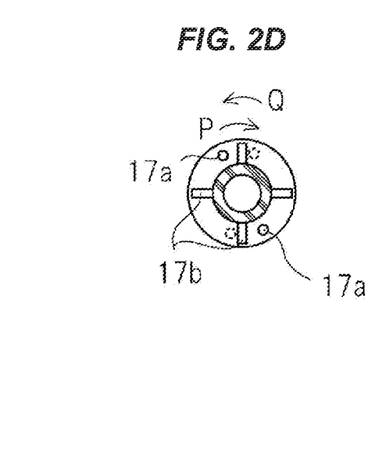

In the first locking mechanism 17, as shown in FIG. 2D as seen from the liquid injection unit 11 side, an end surface of the semispherical projection 17a of the liquid injection unit 11 and an end surface of the operation unit body 10a come close to each other and come into contact by rotating the liquid injection unit 11 in a direction of an arrow P with respect to the operation unit body 10a. Next, the first locking mechanism 17 strongly rotates (tightens) in such a manner that the semispherical projection 17a climbs over the rectangular parallelepiped projection 17b (with deforming) while rotating from a state in which the synthetic resin projections 17a and 17b are in contact, so that the rectangular parallelepiped projection 17b prevents rotation in an inverse direction of an arrow Q to the direction of P for tightening, and the operation unit body 10a and the liquid injection unit 11 can be temporarily fixed.

The term "temporarily fixing" in the present application means a state in which the temporary fixing is not canceled by the rotation during the treatment, but can be canceled by applying a force in the direction of the arrow Q to rotate and allowing the projection 17a to climb over the projection 17b if the cancel is desired.

Next, a description will be given of a second locking mechanism 18 for connecting the sheath connection unit 12 and the liquid injection unit 11.

The second locking mechanism 18 is provided with two semispherical projections 18a which protrude toward the direction of the liquid injection unit 11 from point symmetrical positions on the circumference of the cylindrical end surface in the proximal end side of the sheath connection unit 12, and four rectangular parallelepiped projections 18b which extend radially to the cylindrical end surface which is the level difference portion positioned closer to the proximal end side than the male thread of the liquid injection unit 11 with a longer long side than a diameter of the projection 18a, and protrude toward the direction of the sheath connection unit 12, shown in FIG. 2A.

In the second locking mechanism 18, end surfaces of the semispherical projections 18a of the sheath connection unit 12 comes close to an end surface of the liquid injection unit 11 by rotating and screwing the sheath connection unit 12 with respect to the liquid injection unit 11 in the same manner as the first locking mechanism 17. The second locking mechanism 18 strongly rotates (tightens) in such a manner that the semispherical projection 18a climbs over the rectangular parallelepiped projection 18b (with deforming) while rotating from a state in which the synthetic resin projections 18a and 18b are in contact, so that the rectangular parallelepiped projection 17b prevents rotation in an inverse direction of to the direction for tightening, and the sheath connection unit 12 and the liquid injection unit 11 can be temporarily fixed.

Next, a description will be given of an operation of the treatment tool 1 for the endoscope according to the present embodiment.

Figure 5B:
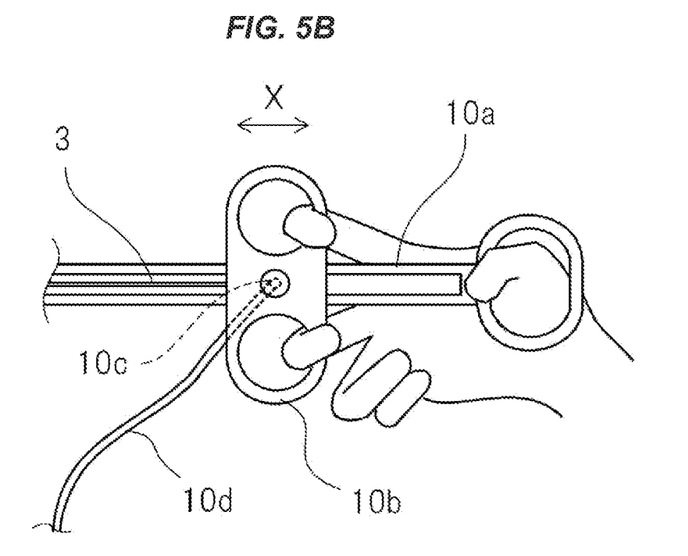

When performing treatment in an affected area, a general right-handed operator faces the back of the right hand to a floor side, puts the thumb on a finger holding portion of the operation unit body 10a, puts the index finger and the middle finger on a finger holding portion of the slider 10b, and moves the operation unit body 10a and the slider 10b relatively in the direction of X in the drawing, in a state in which the power source cord is connected to the power source connection terminal 10c from the floor side, as shown in FIG. 5B, thereby operating the treatment unit which protrudes from the distal end through a channel of the endoscope.

The treatment tool for the endoscope to be operated requires a strong force for feeding the liquid to the distal end through the narrow elongated sheath when feeding the drug solution to the distal end of the sheath. Therefore, the force applied by a non-dominant hand may be insufficient. Thus, the operator switches the operation unit 10 from the dominant hand (right hand) to the non-dominant hand (left hand) to hold while facing the power source connection terminal 10c to the floor side in a state shown in FIG. 5B, holds the injection tool by the dominant hand (right hand), and inserts the distal end of the injection tool into the liquid injection port 11a to inject liquid.

Therefore, the direction of the liquid injection port 11a preferably faces to the right hand side when holding the operation unit by the left hand in a state in which the power source connection terminal 10c faces to the floor side. As shown in FIG. 5A, the direction is preferably set to about 45 degree in a diagonally upward right direction (about 45 degree in a diagonally upward direction in the index finger side when holding by the right hand before supplying liquid), the force of the right hand is easily applied.

[Effect]

As mentioned above, the treatment tool 1 for the endoscope shown in the present embodiment can prevent the screwed portion between the operation unit and the connection unit from being loosened and disconnected, and can temporarily fix the liquid injection port 11a in such a manner that the direction of the liquid injection port 11a do not move from the position where the liquid injection operation mentioned above is easily performed, since the screwed state is temporarily fixed by the locking mechanism. Therefore, the liquid injection operation is easily performed.

Further, the treatment tool 1 for the endoscope shown in the present embodiment is in no danger of damage due to the deterioration of the adhesive agent since no adhesive agent is used for the locking mechanism. Further, in the treatment tool 1 for the endoscope shown in the present embodiment, when a part of the operation unit is damaged, only the operation unit can be replaced by a new operation unit as is different from a case where the adhesive agent is used. Therefore, it is not necessary to draw a whole of the treatment tool for the endoscope from the endoscope during the treatment and replace a whole of the treatment tool, so that a rapid treatment can be achieved, and a cost reduction can be achieved.

Further, in the embodiment shown in FIGS. 2A to 2D mentioned above, there is described the example in which one of the locking mechanism is constructed by four rectangular parallelepiped projections extending in four directions, and the other of the locking mechanism is constructed by two semispherical projections climbing over the rectangular parallelepiped projections. However, the locking mechanism according to the present invention is not limited to the embodiment in the number of the semispherical projections or the rectangular parallelepiped projections. For example, one projection may be constructed by three semispherical projections, and the other projection may be constructed by three rectangular parallelepiped projections extending in three directions, or the other numbers may be employed.

Further, in the embodiment mentioned above, there is described the example in which the first and second locking mechanism have the semispherical shape or the rectangular parallelepiped shape. However, the locking mechanism according to the present invention is not limited to the semispherical shape and the rectangular parallelepiped shape, but may be constructed by the other mechanism, for example, constructed by a combination of one projection and the other groove fitted to the projection.

The invention claimed is:
1. A treatment tool for an endoscope, comprising:
an elongated cylindrical flexible sheath;
an operation wire inserted into a cylinder of the flexible sheath is movable forward and backward in an axial direction within the cylinder by pushing and pulling;
a treatment unit provided in a distal end of the operation wire and performs treatment of an affected area;
an operation unit for operating the operation wire to move forward and backward;
a liquid injection unit arranged between the flexible sheath and the operation unit and provides a liquid injection port for supplying liquid to the treatment unit;

wherein the liquid injection unit and the operation unit are connected by a screw fastening upon relative rotation of the liquid injection unit and the operation unit in respective tightening directions, and a locking mechanism for preventing relative rotation of the liquid injection unit and the operation unit in directions opposite the respective tightening directions to thereby temporarily prevent loosening of the screw fastening during treatment, wherein the locking mechanism comprises:

a first projection arranged in the operation unit and protruding in a direction of the liquid injection unit; and a second projection arranged in the liquid injection unit and protruding in a direction of the operation unit, wherein one of the first or second projections is arranged to pass over the other of the first or second projections as the operation unit and liquid injection unit are rotated in said respective tightening directions during connection of the operation unit and the liquid injection unit, wherein, after connection of the operation unit and the liquid injection unit, the first and second projections engage each other to prevent rotation of the operation unit and liquid injection unit in directions opposite the tightening directions, thereby temporarily preventing loosening of the screw connection during said treatment, wherein one of the first or second projections has a semispherical shape, and wherein the other of the first or second projections has a rectangular parallelepiped shape which has a long side which is longer than a diameter of the semispherical projection, and is provided in one of facing surfaces of the operation unit or the liquid injection unit in such a manner that the long side comes into contact with the semispherical projection during during connection of the operation unit and the liquid injection unit to prevent said loosening of the screw connection during said treatment.

2. The treatment tool for the endoscope according to claim 1, further comprising:

a sheath connection unit arranged between the flexible sheath and the liquid injection unit so as to connect the flexible sheath and the liquid injection unit; and a second locking mechanism which connects the sheath connection unit and the liquid injection unit by screw fastening and temporarily fixes the sheath connection unit to the liquid injection unit.

3. The treatment tool for the endoscope according to claim 2, wherein the second locking mechanism comprises:

a third projection arranged in the sheath connection unit and protruding in a direction of the liquid injection unit; and a fourth projection arranged in the liquid injection unit and protruding toward a direction of the sheath connection unit, wherein one of the third or fourth projections is arranged to pass over the other of the third or fourth projections as the sheath connection unit and the liquid injection unit are relatively rotated in respective sheath and liquid injection unit tightening directions during connection of the sheath connection unit and the liquid injection unit, and wherein, after connection of the sheath connection unit and the liquid injection unit, the third and fourth projections engage each other to prevent relative rotation of the sheath connection unit and the liquid injection unit in directions opposite the sheath and liquid injection unit tightening directions, thereby temporarily preventing loosening of the second screw connection during said treatment.

4. The treatment tool for the endoscope according to claim 3, wherein one of the third or fourth projections has a semispherical shape, and wherein the other of the third or fourth projections has a rectangular parallelepiped shape which has a long side which is longer than a diameter of the semispherical projection, and is provided in one of facing surfaces of the operation unit or the liquid injection unit in such a manner that the long side comes into contact with the semispherical projection during connection of the sheath connection unit and the liquid injection unit to prevent said loosening of the second screw connection during said treatment.

\* \* \* \* \*